US009017735B2

(12) United States Patent
Ghasemzadeh

(10) Patent No.: US 9,017,735 B2
(45) Date of Patent: Apr. 28, 2015

(54) MODULATION OF KCNQ POTASSIUM CHANNEL ACTIVITY FOR TREATMENT OF PSYCHIATRIC DISORDERS AND THE SYMPTOMS THEREOF

(75) Inventor: Mohammadhossein Behnam Ghasemzadeh, Cedarburg, WI (US)

(73) Assignee: Marquette University, Milwaukee, WI (US)

( * ) Notice: Subject to any disclaimer, the term of this patent is extended or adjusted under 35 U.S.C. 154(b) by 627 days.

(21) Appl. No.: 12/793,330

(22) Filed: Jun. 3, 2010

(65) Prior Publication Data
US 2010/0310681 A1 Dec. 9, 2010

Related U.S. Application Data
(60) Provisional application No. 61/217,706, filed on Jun. 3, 2009.

(51) Int. Cl.
*A61K 31/444* (2006.01)
*A61K 31/451* (2006.01)
*A61K 31/454* (2006.01)
*A61K 31/496* (2006.01)
*A61K 31/519* (2006.01)
*A61K 31/53* (2006.01)
*A61K 31/5415* (2006.01)
*A61K 31/5513* (2006.01)
*A61K 31/554* (2006.01)
*A61K 33/00* (2006.01)
*A61P 25/00* (2006.01)
*A61P 25/18* (2006.01)
*A61P 25/36* (2006.01)
*A61K 31/4427* (2006.01)
*A61K 31/122* (2006.01)
*A61K 31/4025* (2006.01)
*A61K 31/4409* (2006.01)
*A61K 31/4725* (2006.01)

(52) U.S. Cl.
CPC .......... *A61K 31/4427* (2013.01); *A61K 31/122* (2013.01); *A61K 31/4025* (2013.01); *A61K 31/4409* (2013.01); *A61K 31/4725* (2013.01)

(58) Field of Classification Search
CPC ............ A61K 31/122; A61K 31/4025; A61K 31/4409; A61K 31/4427; A61K 31/4725; A61K 2300/00
See application file for complete search history.

(56) References Cited

U.S. PATENT DOCUMENTS

| 6,262,081 | B1 * | 7/2001 | Zaczek ........................ 514/332 |
| 2006/0063790 | A1 | 3/2006 | Gillman et al. | |
| 2006/0155121 | A1 * | 7/2006 | Tornoe et al. ................. 540/601 |
| 2007/0129403 | A1 * | 6/2007 | Smith et al. .................... 514/337 |

FOREIGN PATENT DOCUMENTS

| JP | 2006514917 A | 5/2006 |
| JP | 2008524999 A | 7/2008 |
| WO | 0044786 | 8/2000 |
| WO | 0134161 | 5/2001 |
| WO | 0200217 | 1/2002 |
| WO | 2004004660 A2 | 1/2004 |
| WO | 2006067056 A1 | 6/2006 |

OTHER PUBLICATIONS

Zaczek, The Journal of Pharmacology and Experimental Therapeutics, 285, 2.*
Schnee, The Journal of Pharmacology and Experimental Therapeutics, 286, 2, 1998.*
Yoshida, J Neurophysiol, 98, 2007.*
Coghlan, The Journal of Medicinal Chemistry, 44, 2001.*
Peuskens, Acta Psychiatr Scand, 96, 1997.*
Beveridge, Philosophical Transactions of The Royal Society, B, 12, 2008.*
Carol, Psychiatric Services, 52, 8, 2001.*
Bakshi et al., "Phencyclidine-Induced Deficits in Prepulse Inhibition of Startle are Blocked by Prazosin, an Alpha-1 Noradrenergic Antagonist", Journal of Pharmacology and Experimental Therapeutics, 1997, 283, 666-674.
Bal et al., "Homomeric and Heteromeric Assembly of KCNQ (Kv7) K+ Channels Assayed by Total Internal Reflection Fluorescence/ Fluorescence Resonance Energy Transfer and Patch Clamp Analysis", Journal of Biological Chemistry, 2008, 283, 30668-30676.
Brown et al., "Muscarinic Suppression of a Novel Voltage-Sensitive K+ Current in a Vertebrate Neurone", Nature, 1980, 283, 673-676.
Brown, "Kv7 (KCNQ) Potassium Channels that are Mutated in Human Diseases", Journal of Physiology, 2008, 1781-1783.
Earl et al., "2-Fluoro-4-pyridinylmethyl Analogues of Linopirdine as Orally Active Acetylcholine Release-enhancing Agents with Good Efficacy and Duration of Action", Journal of Medicinal Chemistry, 1998, 41, 4615-4622.
Elmedyb et al., "Modulation of ERG Channels by XE991", Basic & Clinical Pharmacology & Toxicology, 2007, 100, 316-322.
Fenton et al., "Natural History of Shizophrenia Subtypes. II. Positive and Negative Symptoms and Long-term Course", Archives of General Psychiatry, 1991, 48, 978-986.
Gribkoff, "The Therapeutic Potential of Neuronal KCNQ Channel Modulators", Expert Opin. Ther. Targets, 2003, 7 (6), 737-748.
Gribkoff, "The Therapeutic Potential of Neuronal Kv7 (KCNQ) Channel Modulators: An Update", Expert Opin. Ther. Targets, 2008, 12(5), 565-581.
Jentsch, "Neuronal KCNQ Potassium Channels: Physiology and Role in Disease", Nature Reviews, 2000, 1, 21-30.
Jia et al., "NGF Inhibits M/KCNQ Currents and Selectively Alters Neuronal Excitability in Subsets of Sympathetic Neurons Depending on their M/KCNQ Current Background", Journal of General Physiology, 2008, 131, 575-587.
Kasten et al., "Differential Regulation of Action Potential Firing in Adult Murine Thalamocortical Neurons by Kv3.2, Kv1, and SK Potassium and N-type Calcium Channels", 2007, 565-582.

(Continued)

*Primary Examiner* — Robert A Wax
*Assistant Examiner* — William Craigo
(74) *Attorney, Agent, or Firm* — Andrus Intellectual Property Law, LLP

(57) ABSTRACT

Disclosed herein are compositions and methods for treating a psychiatric disorder or symptoms thereof in a patient. The compositions comprise a compound that modulates KCNQ (Kv7) potassium channel activity and the methods include administering an effective amount of the compound that modulates KCNQ (Kv7) potassium channel activity.

14 Claims, 5 Drawing Sheets

(56) References Cited

OTHER PUBLICATIONS

Lieberman et al., "Effectiveness of Antipsychotic Drugs in Patients with Chronic Schizophrenia", New England Journal of Medicine, 2005, 353, 1209-1223.
Robbins, "KCNQ Potassium Channels: Physiology, Pathophysiology, and Pharmacology", Pharmacology & Therapeutics, 2001, 1-19.
Saganich et al., "Differential Expression of Genes Encoding Subthreshold-operating Voltage-gated K+ Channels in Brain", Journal of Neuroscience, 2001, 21, 4609-4624.
Smith et al., "Oral Dual-Ion Channel Blocker HP184 Improves Locomotor Scores and Myelination in Rats with Spinal Cord Injury", Society for Neuroscience—Abstract Archive: 2003.
Tam, "Naloxone-inaccessible Sigma Receptor in Rat Central Nervous System", Proceedings of the National Academy of Sciences, 1983, 80, 6703-6707.
Tam et al., "Novel Receptor Site Involved in Enhancement of Stimulus-induced Acetylcholine, Dopamine, and Serotonin Release", Molecular Pharmacology, 1991, 40, 16-21.
Wang et al., "Positional Cloning of a Novel Potassium Channel Gene: KVLQT1 Mutations Cause Cardiac Arrhythmias", Nature Genetics, 1996, 12, 17-23.
Wang et al., "KCNQ2 and KCNQ3 Potassium Channel Subunits: Molecular Correlates of the M-channel", Science, 1998, 282, 1890-1983.
Wang et al., "Molecular Basis for Differential Sensitivity of KCNQ and I(Ks) Channels to the Cognitive Enhancer XE991", Molecular Pharmacology, 2000, 57, 218-1223.
Wladyka et al., "KCNQ/M—currents Contribute to the Resting Membrane Potential in Rat Visceral Sensory Neurons", Journal of Physiology, 2006, 175-189.
Wu et al., "Coupling of L-Type Ca2+ Channels to Kv7/KCNQ Channels Creates a Novel, Activity-Dependent, Homeostatic Intrinsic Plasticity", Journal of Neurophysiology, 2008, 100, 1897-1908.
Wulff et al., "Voltage-gated Potassium Channels as Therapeutic Drug Targets", Nat. Rev. Drug Discov., 2009, 8(12): 982-1001.
Xiong et al., "Activation of Kv7 (KCNQ) Voltage-gated Potassium Channels by Synthetic Compounds", Cell Press, 2007, 99-107.
Sotty et al., "Antipsychotic-like effect of retigabine [N-(2-amino-4-(fluorobenzylamino)-phenyl)carbamic acid ester], a KCNQ potassium channel opener, via modulation of mesolimbic dopaminergic neurotransmission", Journal of Pharmacology and Experimental Therapeutics, Mar. 2009, 328(3):951-962.
European Search Report for EP10784089 dated Oct. 10, 2012.
Ferrante et al., "Computational Models of Neuronal Biophysics and the Characterization of Potential Neuropharmacological Targets," Current Medicinal Chemistry, 2008,15:2456-2471.
Miceli et al., "Molecular Pharmacology and Therapeutic Potential of Neuronal Kv7-Modulating Drugs," ScienceDirect, Current Opinion in Pharmacology, 2008, 8:65-74.
Adams et al., "Corticolimbic dopamine neurotransmission is temporally dissociated from the cognitive and locomotor effects of phencyclidine", J Neurosci, 1998,18:5545-5554.
Aisen et al., "3,4-diaminopyridine as a treatment for amyotrophic lateral sclerosis", J Neurol Sci, 1995, 129:21-24.
Amato et al., "Are there protective treatments for cognitive decline in MS?" 2006, J Neurol Sci, 245:183-186.
Beninger et al., "Physostigmine, but not 3,4-diaminopyridine, improves radial maze performance in memory-impaired rats," Pharmacol Biochem Beha, 1995, 51:739-746.
Bramness et al., "Amphetamine-induced psychosis—a separate diagnostic entity or primary psychosis triggered in the vulnerable?" BMC Psychiatry, 2012, 12:221.
Buchanan et al., "A Summary of the FDA-NIMH-MATRICS Workshop on Clinical Trials Design for Neurocognitive Drugs for Schizophrenia", Schizophrenia Bulletin, 2005, 31(1):5-19.
Cassel et al., "Cognitive deficits in aged rats correlate with levels of L-arginine, not with nNOS expression or 3,4-DAP-evoked transmitter release in the frontoparietal cortex", Eur Neuropsychopharmacol, 2005, 15:163-175.

Chandy et al., "K+ channels as targets for specific immunomodulation", Trends in Pharmacological Sciences, May 2004, 25(5): 280.
Cheung et al., "Discovery of a Series of 2-Phenyl-N-(20(pyrrolidin-1-yl)phenyl)acetamides as Novel Molecular Switches that Modulate Modes of Kv7.2 (KCNQ2) Channel Pharmacology: Identification of (S)-2-Phenyl-N-(2-(pyrrolidin-1-yl)phenyl)butanamide (ML252) as a Potent, Brain Penetrant Kv7.2 Channel Inhibitor", Journal of Medicinal Chemistry, 2012, 55: 6975-6979.
Day et al., "Cocaine-induced increase in cortical acetylcholine release: interaction with the hypothalamo-pituitary-adrenal axis", Eur J Neurosci, 1997, 9:1130-1136.
Earl et al., "2-Fluoro-4-pyridinylmethyl Analogues of Linopirdine as Orally Active Acetylcholine Release-Enhancing Agents with Good Efficacy and Duration of Action", J. Med. Chem., 1998, 41:4615-4622.
Ellenbroeck, "Psychopharmacological treatment of schizophrenia: What do we have, and what could we get?" Neuropharmacology, 2012, 62:1371-1380.
Gao et al., "Isoform-specific Prolongation of Kv7 (KCNQ) Potassium Channel Opening Mediated by New Molecular Determinants for Drug-Channel Interactions", The Journal of Biological Chemistry, Sep. 3, 2010, 285 (36):28322-28332.
Gray et al., "The pipeline and future of drug development in schizophrenia", Molecular Psychiatry, 2007, 12:904-922.
Hanson et al., "UK-78,282, a novel piperidine compound that potently blocks the Kv1.3 voltage-gated potassium channel and inhibits human T cell activation", British Journal of Pharmacology, 1999, 126: 1707-1716.
Hermens et al., "Amphetamine psychosis: a model for studying the onset and course of psychosis", Med J Aust, 2009, 190(4 Suppl):S22-S25.
Hows et al., "High-performance liquid chromatography/tandem mass spectrometric assay for the simultaneous measurement of dopamine, norepinephrine, 5-hydroxytryptamine and cocaine in biological samples. J Neurosci Methods", 2004, 138:123-132.
Jensen et al., "Neuronal Nicotinic Acetylcholine Receptors: Structural Revelations, Target Identifications, and Therapeutic Inspirations", Jul. 28, 2005, 48(15): 4705.
Jentsch et al., "The neuropsychopharmacology of phencyclidine: from NMDA receptor hypofunction to the dopamine hypothesis of schizophrenia", Neuropsychopharmacology, 1999, 20:201-225.
Laughren et al., "Food and drug administration perspective on negative symptoms in schizophrenia as a target for drug treatment claim", Schizophrenia Bulletin, 2006, 32(2):220-222.
Lauth et al., "3,4-Diaminopyridine-evoked noradrenaline release in rat hippocampal slices: facilitation by endogenous or exogenous nitric oxide", Brain Res, 1995 692:174-182.
Ries et al. "Properties of 3,4-diaminopyridine-evoked dopamine and acetylcholine release in rabbit caudate nucleus slices: involvement of facilitatory adenosine A2 receptors or nitric oxide?" Brain Res, 1996, 743:303-314.
Schmalhofer et al., "Identification of a New Class of Inhibitors of the Voltage-Gated Potassium Channel, Kv1.3, with Immunosuppressant Properties", Biochemistry, 2002, 41: 7781-7794.
Schmalhofer et al., "Di-substituted cyclohexyl derivatives bind to two identical sites with positive cooperativity on the voltage-gated potassium channel, Kv1.3", Biochemistry, 2003, 42:4733-4743.
Schmalhofer et al., "A Kv2.1 gating modifier binding assay suitable for high throughput screening", Channels, Nov./Dec. 2009, 3(6):437-447.
Schmitz et al., "Design of PAP-1, a Selective Small Molecule Kv1.3 Blocker, for the Suppression of Effector Memory T Cells in Autoimmune Diseases", Molecular Pharmacology, 2005, 68:1254-1270.
Thomsen et al., "Effects of 4-aminopyridine and 3,4-diaminopyridine on transmitter release at the neuromuscular junction", J Pharmacol Exp Ther, 1983, 227:260-265.
Xiong et al., "Zinc pyrithione-mediated activation of voltage-gated KCNQ potassium channels rescues epileptogenic mutants", Nature Chemical Biology, May 2007, 3(5): 287.

* cited by examiner

MODULATION OF KCNQ POTASSIUM CHANNEL ACTIVITY FOR TREATMENT OF PSYCHIATRIC DISORDERS AND THE SYMPTOMS THEREOF

CROSS-REFERENCE TO RELATED APPLICATIONS

The present application claims the benefit under 35 U.S.C. §119(e) to U.S. Provisional Application No. 60/217,706, filed on Jun. 3, 2009, the contents of which are incorporated herein by reference.

STATEMENT REGARDING U.S. GOVERNMENT SPONSORED RESEARCH OR DEVELOPMENT

This invention was made with U.S. government support under Grant No. DA14328 from the National Institute on Drug Abuse. The U.S. government has certain rights in this invention.

BACKGROUND

The field of the present invention relates to compositions and methods for treating psychiatric conditions associated with KCNQ potassium channels and the symptoms thereof. In particular, the field of the invention relates to compositions and methods for treating schizophrenia, drug addiction, and the symptoms thereof.

Schizophrenia and addiction are complex brain disorders with unknown etiology. Despite decades of intensive research, the neurological underpinnings of these devastating human pathologies remain unknown. Recent advances have suggested that pathological plasticity in dopamine and glutamate signaling in the brain regions including, but limited to, prefrontal cortex, caudate putamen, nucleus accumbens, and ventral tegmental area may be involved. Therefore, treatments capable of modulating dopaminergic and glutamatergic neurotransmission and signaling in the brain may be beneficial in ameliorating the cellular and molecular pathologies and the behavioral symptoms in these psychiatric disorders.

Schizophrenia and addiction are complex brain disorders and display a variety of behavioral symptoms. Individual treatments may be able to address only a subset of the symptoms associated with these behavioral phenotypes. For example, some available medications for schizophrenia may treat the positive symptoms of the disease in absence of any significant effects on the negative or cognitive symptoms. Therefore, there is a need to discover and develop effective medications for these additional symptoms. In addition, currently prescribed medications for the treatment of these disorders have significant shortcomings such as inadequate efficacy and/or significant side effects such as weight gain, sexual dysfunction, motor deficits, cardiovascular irregularities, increased risk for diabetes and sudden death.

In regard to substance abuse and addiction, it was estimated that approximately 23.6 million Americans aged 12 were in need of treatment in 2006. The annual cost of drug abuse to society in the United States is more than $181 billion which when combined with healthcare, criminal justice, and lost productivity may exceed $500 billion. While individuals addicted to opiates such as opium and heroin may benefit from pharmacological treatments such as methadone and buprenorphine, there is no medication for the treatment of those addicted to psychostimulants such as cocaine and methamphetamine. The lack of an effective treatment for psychostimulant addiction highlights the need to discover and develop new, novel, and effective medications for treating psychostimulant addiction and the symptoms thereof.

As disclosed herein, KCNQ (Kv7) potassium channel activity may be targeted to treat psychiatric disorders such as schizophrenia, drug addiction, and the symptoms thereof. Known drugs that modulate KCNQ (Kv7) potassium channel activity may be utilized in treatment methods, and further, new drugs that modulate KCNQ (Kv7) potassium channel activity may be identified and developed.

SUMMARY

Disclosed herein are compositions and methods for treating a psychiatric disorder or symptoms thereof in a patient. The compositions comprise a compound that modulates KCNQ (Kv7) potassium channel activity and the methods include administering an effective amount of the compound that modulates KCNQ (Kv7) potassium channel activity.

In some embodiments, the compound inhibits KCNQ (Kv7) potassium channel activity. For example, the compound may block or close a KCNQ (Kv7) potassium channel (e.g., as determined by observing a decrease in flow of potassium ions through the channel). In some embodiments of the methods, the compound is administered in order to deliver an effective concentration of the compound for closing the KCNQ (Kv7) potassium channel (e.g., in neurological tissue).

The compositions and methods are effective for treating a patient having a psychiatric disorder or symptoms thereof. In some embodiments, the patient has schizophrenia and the disclosed compositions and methods are effective for treating one or more negative symptoms of schizophrenia in the patient. Negative symptoms include, but are not limited to, flat effect, lack of motivation, anhedonia, diminished speech, social withdrawal, lack of energy, and apathy.

In some embodiments, the compositions include and the methods utilize compounds that inhibit KCNQ (Kv7) potassium channel activity. Suitable inhibitors of KCNQ (Kv7) potassium channel activity may include Linopirdine (3,3-bis(4-pyridinylmethyl)-1-phenylindolin-2-one), XE991 (10,10-bis(4-pyridinylmethyl)-9(101-1)-anthracenone), DMP543 (10,10-bis(2-fluoro-4-pyridinylmethyl)-9(10H)-anthracenone), and other compounds, analogs, or derivatives as disclosed herein.

The compositions may include and the methods may utilize the inhibitor of KCNQ (Kv7) potassium channel activity as a single active ingredient, or the compositions may include and the methods may utilize a second compound as an active ingredient. For example, the compositions may include and the methods may utilize a first active ingredient that treats a negative symptom of schizophrenia and a second active ingredient that treats a negative symptom or another type of symptom of schizophrenia (e.g., a positive symptom or a cognitive symptom of schizophrenia). In some embodiments, the methods include administering an effective amount of a second compound for treating a psychiatric disorder selected from a group selected from chlorpromazine, haloperidol, fluphenazine, promazine, clozapine, sertindole, amisulpride, zotepine, paliperidone, risperidone, aripiprazole, lamotrigine, quetiapine, perphenazine, flupenthixol, ziprasidone, olanzapine, lithium, and valproic acid. The second compound may be administered before, concurrently with, or after the compound that inhibits KCNQ (Kv7) potassium channel activity. For example, the second compound may be administered before the compound that inhibits KCNQ (Kv7) potassium channel activity, and the compound that inhibits KCNQ (Kv7) potassium channel activity may be administered to the patient after the patient becomes refractory to treatment with the second compound. In methods where the compound that inhibits KCNQ (Kv7) potassium channel activity and the second compound are administered concurrently, the two compounds may be formulated together as a single pharmaceutical composition and administered as a single pharmaceutical composition. Alternatively, the compound that inhibits KCNQ (Kv7) potassium channel activity and the second compound may be formulated as separate pharmaceutical compositions that are administered concurrently.

In further embodiments of the methods, the patient having a psychiatric disorder is a patient that is addicted to a psychostimulant such as cocaine or methamphetamine. The compound that modulates KCNQ (Kv7) potassium channel activity may include a compound that inhibits KCNQ (Kv7) potassium channel activity (e.g., Linopirdine, XE991, DMP543, and other compounds, analogs, or derivatives as disclosed herein). In some embodiments of the disclosed methods, the compound may be administered to the patient having an addiction in an effective amount for treating the addiction or a symptom thereof such as craving.

Also disclosed herein are methods for screening for compounds to treat psychiatric disorders associated with KCNQ potassium channel activity. For example, compounds that are identified as modulators of KCNQ potassium channel activity in vitro (e.g., as determined by measuring an increase or decrease in a potassium current through the channel when the compound is present) may be selected as candidate compounds for treating psychiatric disorders associated with KCNQ potassium channel activity. In another example, compounds that are capable of displacing a channel binding compound (optionally labeled with a fluorophore or an isotope) may be selected as candidate compounds for treating psychiatric disorders associated with KCNQ (Kv7) potassium channel activity.

DETAILED DESCRIPTION

Figure 1:
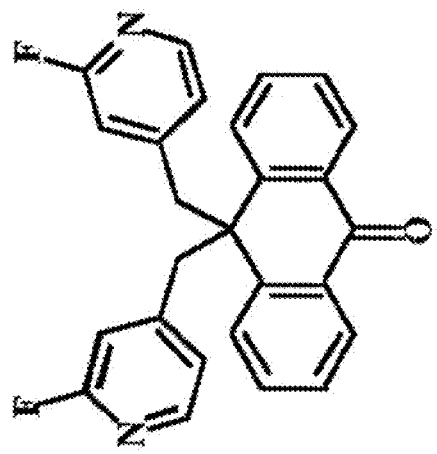
FIG. 1. Molecular structures of Linopirdine, XE991, and DMP543.
Figure 1:
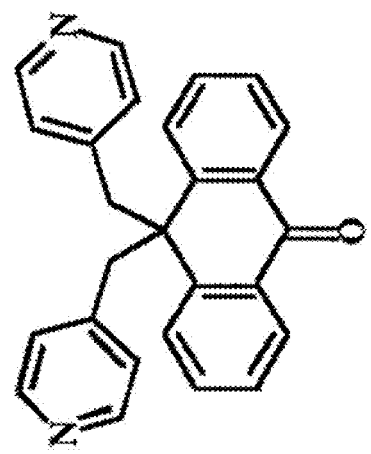
Figure 1:
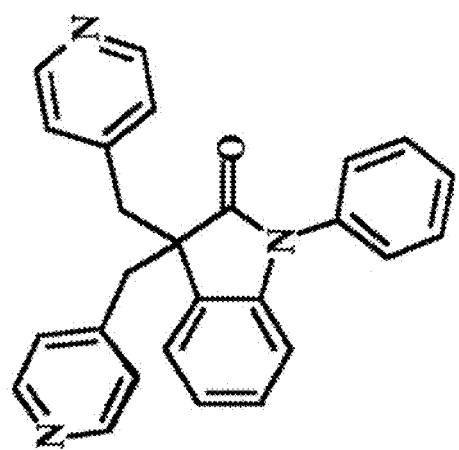

Disclosed are compositions and methods for treating psychiatric disorders or the symptoms thereof associated with KCNQ (Kv7) potassium channel activity. The disclosed subject matter further may be described utilizing terms as defined below.

Unless otherwise specified or indicated by context, the terms "a", "an", and "the" mean "one or more." In addition, singular nouns such as "negative symptom" and "cognitive symptom" should be interpreted to mean "one or more cognitive symptoms" and "one or more non-target proteins," unless otherwise specified or indicated by context.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising."

The terms "patient" and "subject" may be used interchangeably herein. A patient may be a human patient. A patient may refer to a human patient having or at risk for acquiring a psychiatric disorder associated with KCNQ (Kv7) potassium channel activity, which may include, but is not limited to, schizophrenia, drug addiction, schizoaffective disorder, schizophreniform disorder, schizoid personality disorder, schizotypal personality disorder, bipolar disorder, post-traumatic stress disorder (PTSD), and major depressive disorder (depression).

Schizophrenia, as utilized herein, refers to psychiatric disorder that affects about 1.1% of world population over the age of 18 years. In the United States, there are more than 3 million individuals that suffer from schizophrenia in any given year. Schizophrenia is a chronic, severe, and disabling brain disorder that typically has its clinical onset in late teens through thirties with an earlier age of onset for men than women. Once the clinical symptoms occur, the disease persists, in most cases, throughout life. The symptoms of schizophrenia can be organized into three categories. The "positive symptoms" are psychotic behaviors not seen in healthy individuals and include hallucinations, delusions, thought disorders, disorganized speech, and movement disorders. The "negative symptoms" are associated with emotions and behaviors that are diminished or absent in schizophrenia patients and include flat affect, lack of motivation, anhedonia, diminished speech, social withdrawal, lack of energy, and apathy. The "cognitive symptoms" relate to diminished cognitive function and loss of memory and include poor executive function, loss of attention and focus, deficits in perception, difficulty in learning, working memory deficits, and problems with short- and long-term memory. The patients suffer from all three categories of symptoms although it may not be to the same extent at all times. Typically, the positive symptoms ameliorate by age while the negative and cognitive abnormalities, in most cases, are consistently present or may even exacerbate with age.

There is no cure for schizophrenia and the available medications and behavioral treatments aim at managing symptoms of the disease. The available medications can be divided into two classes. The first generation of antipsychotics or "the typical antipsychotics" were first discovered in 1950s and are effective in treatment of positive symptoms but are not effective against the negative and cognitive symptoms. Examples of the typical antipsychotics include Chlorpromazine (Thorazine) and Haloperidol (Haldol). These medications display significant side effects ranging from Parkinsonian movement disorders, sexual dysfunction, to metabolic abnormalities such as weight gain, increase in blood cholesterol, and increased risk for diabetes. The lack of efficacy against the negative and cognitive symptoms, severity of side effects and patient noncompliance prompted the research leading to discovery of the second generation of the antipsychotics or "the atypical antipsychotics." Clozapine was the first atypical antipsychotic discovered in the early 1970s. These medications display reduced movement side effects but suffer from side effects such as weight gain and other metabolic side effects. In addition, recent studies have shown that the second generation atypical antipsychotics have little or no advantage over the first generation typical antipsychotics in treating the negative and cognitive symptoms. A recent study showed that about 75% of schizophrenia patients on both types of antipsychotic medications are non-compliant after 18 months (Lieberman et al., (2005) The New England Journal of Medicine, vol. 353, pp. 1209-1223). Therefore, there is an acute and significant need for new medications that can treat schizophrenia symptoms with no or little side effects. This is especially true of the treatments for the negative and cognitive symptoms as current medications are not effective.

Addiction, as utilized herein, refers to a psychiatric disorder that is characterized by transition from recreational to compulsive use of drugs and appearance of uncontrollable drug craving. Once this transition has taken place, drug craving will persist for an extended period of time despite abstinence from drug use. During abstinence, exposure to drug associated cues, stress, or the drug itself will result in relapse to drug use.

A patient may refer to a human patient having or at risk for acquiring one or more symptoms of a psychiatric disorder associated with KCNQ (Kv7) potassium channel activity. Symptoms of schizophrenia may include but are not limited to "negative symptoms," as discussed herein, where the KCNQ (Kv7) potassium channel activity inhibitor is administered to reduce or prevent negative symptoms in the patient. Symptoms of drug addiction may include craving, for example, where the patient is addicted to a psychostimulant, such as cocaine or methamphetamine, and the KCNQ (Kv7) potassium channel activity is administered to reduce craving for cocaine or methamphetamine in the patient.

The present methods relate to treatment of psychiatric disorders associated with KCNQ (Kv7) potassium channel activity. The "KCNQ potassium channels" alternatively referred to as the "Kv7 channels" are a small family of voltage-gated potassium channel subunits that are encoded by the KCNQ genes (KCNQ1-5). (See, e.g., Robbins, J. (2001). Pharmacol. Ther, 90, 1-19; and Jentsch T. J. (2000) Nat. Rev. Neurosci. 1, 21-30, the contents of which are incorporated by reference in their entireties). Modulation of KCNQ potassium channel activity has been suggested to have therapeutic potential. (See, e.g., Wulff et al., Nature Reviews, Drug Discovery, Volume 8, Pages 982-1001, December 2009; Brown, J. Physiol. 586.7 (2008) pp 1781-1783; Gribkoff, Expert Opin. Ther. Targets (2008) 12(5):565-581; Xiang et al., Trends in Pharmacological Sciences, 2007, 29(2), pages 99-107; and Gribkoff, Expert Opin. Ther. Targets (2003) 7(6): 737-748; the content of which is incorporated herein by reference in their entireties). However, the present inventor is unaware of any prior teaching or suggestion that the inhibition of KCNQ potassium channel activity may be utilized in a therapeutic method for treating the negative symptoms of schizophrenia or in a therapeutic method for treating craving in a drug addict.

Suitable compounds for the methods contemplated herein modulate KCNQ (Kv7) potassium channel activity, such as compounds that inhibit or alternatively activate or enhance KCNQ (Kv7) potassium channel activity. Suitable compounds may inhibit KCNQ (Kv7) potassium channel activity by blocking, closing, or otherwise inhibiting a KCNQ (Kv7) potassium channel from facilitating passage of ions from one side of a membrane to the other side of the membrane in which the KCNQ (Kv7) potassium channel is present. KCNQ (Kv7) potassium channel activity and modulation thereof, including inhibition thereof, may be assessed by methods described in the art (e.g., patch clamp analysis, see, e.g., Bal et al, J. Biol. Chem. 2008 283(45):30668-30676; Wu et al., J. Neurophysiol. 2008 100(4); 1897-1908; Kasten et al., J. Physiol. 2007 584(Pt. 2):565-582; Jia et al., J. Gen Physiol. 2006 131(6):575-587; and Wladyka et al., J. Physiol. 2006 584(Pt. 1):175-189; the contents of which are incorporated by reference in their entireties). The compounds utilized in the methods herein may bind to one or more proteins of the KCNQ (Kv7). In some embodiments, the compounds utilized in the methods herein bind to one or more of the KCNQ2 protein and the KCNQ3 protein, thereby modulating KCNQ (Kv7) potassium channel activity.

Compounds that modulate KCNQ (Kv7) potassium channel activity are known in the art and may include KCNQ (Kv7) potassium channel activity inhibitors or alternatively KCNQ (Kv7) potassium channel activity activators. KCNQ (Kv7) potassium channel activity inhibitors may include but are not limited to Linopirdine (Dupont), XE991 (Dupont), DMP543 (Dupont), d-tubocurarine, verapamil, 4-aminopurine, Azimilide (Proctor and Gamble), MHR-1556 (Sanofi-Aventis), and L-768673 (Merck). KCNQ (Kv7) potassium channel activators or openers may include but are not limited to retigabine (N-(2-amino-4-(fluorobenzylamino)-phenyl) carbamic acid ester), flupirtine, ICA-27243 (Icagen), ICA-105665 (Icagen), Maxipost (BMS-204352), diclofenac, NH6, zinc pyrithione, niflumic acid, mefenamic acid, and L364373 (Merck). These compounds and other compounds that modulate KCNQ (Kv7) channel activity are disclosed in Wulff et al., Nature Reviews, Drug Discovery, Volume 8, Pages 982-1001, December 2009 (the content of which is incorporated herein by reference in its entirety).

A suitable compound for the methods contemplated herein may include Linopirdine or analogs or derivatives thereof (e.g., analogs or derivatives thereof that inhibit KCNQ (Kv7) potassium channel activity). Referring to the PubChem Database provided by the National Center for Biotechnology Information (NCBI) of the National Institute of Health (NIH), Linopirdine is referenced by compound identification (CID) number 3932 (which entry is incorporated herein by reference in its entirety). (See also FIG. 1.) Analogs or derivative of Linopirdine may include salts, esters, amides, or solvates thereof. Furthermore, analogs or derivatives of Linopirdine may include "similar compounds" or "conformer compounds" as defined at the PubChem Database, which include but are not limited to compounds referenced by CID Nos.: 11015296, 10993167, 454643, 454641, 45114239, 23581818, 14209557, 14209555, 14209553, 10549571, 9832106, 14209556, 10764944, 454654, 19438999, 14960217, 14209554, 11823673, 14209559, 15284399, 19438967, 19438958, 19438948, 19438961, 9865313, 19104987, 15296097, 19438997, 15346939, 11823673, 15284397, 15296101, 15284414, and 10476777, which entries are incorporated herein by reference in their entireties. Preferably, effective concentrations of Linopirdine or analogs and derivatives of Linopirdine treat negative symptoms in a patient having schizophrenia. Preferably, effective concentrations of Linopirdine or analogs and derivatives of Linopirdine treat craving in a patient having drug addiction.

A suitable compound for the methods contemplated herein may include XE991 or analogs or derivatives thereof (e.g., analogs or derivatives thereof that inhibit KCNQ (Kv7) potassium channel activity). Referring to the PubChem Database provided by the National Center for Biotechnology Information (NCBI) of the National Institute of Health (NIH), XE991 is referenced by compound identification (CID) number 656732 (which entry is incorporated herein by reference in its entirety). (See also FIG. 1.) Analogs or derivative of XE991 may include salts, esters, amides, or solvates thereof. Furthermore, analogs or derivatives of XE991 may include "similar compounds" or "conformer compounds" as defined at the PubChem Database, which include but are not limited to compounds referenced by CID Nos.: 45073462, 17847140, 11122015, 19922429, 19922428, 15678637, 328741, 45234820, 45053849, 45053848, 42194630, 42194628, 21537929, 19922433, 14941569, 15678632, and 409154, which entries are incorporated herein by reference in their entireties. Derivatives or analogs of XE991 may include a deuterated derivative or analog, for example, having a formula:

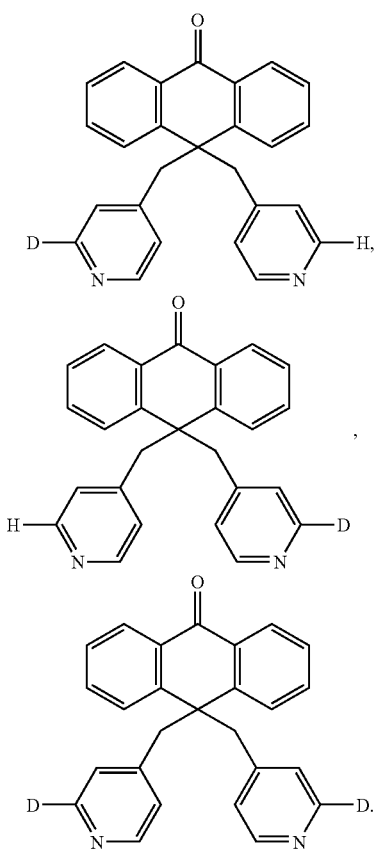

Preferably, effective concentrations of XE991 or analogs and derivatives of XE991 treat negative symptoms in a patient having schizophrenia. Preferably, effective concentrations of XE991 or analogs and derivatives of XE991 treat craving in a patient having drug addiction.

A suitable compound for the methods contemplated herein may include DMP543 or analogs or derivatives thereof (e.g., analogs or derivatives thereof that inhibit KCNQ (Kv7) potassium channel activity). Referring to the PubChem Database provided by the National Center for Biotechnology Information (NCBI) of the National Institute of Health (NIH), DMP543 is referenced by compound identification (CID) number 9887884 (which entry is incorporated herein by reference in its entirety). (See also FIG. 1.) Analogs or derivative of DMP543 may include salts, esters, amides, or solvates thereof. Furthermore, analogs or derivatives of DMP543 may include "similar compounds" or "conformer compounds" as defined at the PubChem Database, which include but are not limited to compounds referenced by CID Nos.: 9801773, 10644338, 9930525, 19606104, 10926895, 10093074, 10093073, 45194349, 19606090, 19606069, 19606087, 19606071, 19606104, 19606084, 19606108, 19606110, 19606109, and 15296110, which entries are incorporated herein by reference in their entireties. Derivatives or analogs of DMP543 may include a deuterated derivative or analog, for example, having a formula:

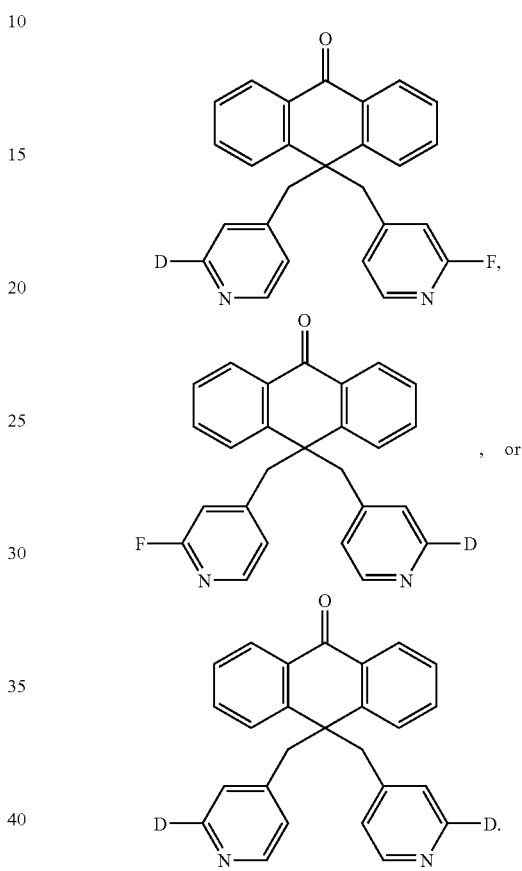

Preferably, effective concentrations of DMP543 or analogs and derivatives of DMP543 treat negative symptoms in a patient having schizophrenia. Preferably, effective concentrations of DMP543 or analogs and derivatives of DMP543 treat craving in a patient having drug addiction.

In some embodiments, the compounds utilized in the methods disclosed herein may have one or more chiral centers, and the use of stereoisomers, epimers, and enantiomers of the compounds in the disclosed methods are contemplated. The compounds may be optically pure with respect to one or more chiral centers (e.g., some or all of the chiral centers may be completely in the S configuration; some or all of the chiral centers may be completely in the R configuration; etc.). Additionally or alternatively, one or more of the chiral centers may be present as a mixture of configurations (e.g., a racemic or another mixture of the R configuration and the S configuration). Use of compositions comprising substantially purified stereoisomers, epimers, or enantiomers of compound are contemplated herein (e.g., a composition comprising at least about 90%, 95%, or 99% pure stereoisomer, epimer, or enantiomer may be administered in the methods contemplated herein.)

Pharmaceutically acceptable salts of the compounds are contemplated and also may be utilized in the disclosed methods. For example, a carboxylic acid group of the disclosed compounds may be deprotonated and an amino group of the disclosed compounds may be protonated. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-1,4-dioate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

It should be recognized that the particular counter-ion forming a part of any salt of a compound disclosed herein is usually not of a critical nature, so long as the salt as a whole is pharmacologically acceptable and as long as the counterion does not contribute undesired qualities to the salt as a whole. Undesired qualities may include undesirably solubility or toxicity.

It will be further appreciated that the disclosed compounds can be in equilibrium with various inner salts. For example, inner salts include salts wherein the compound includes a deprotonated carboxyl group and a protonated amino group.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The methods disclosed herein may be practiced in vitro or in vivo. More particularly, the methods disclosed herein may be used in vivo to treat the symptoms of a patient having a psychiatric disorder associated with KCNQ (Kv7) potassium channel activity. Details with regard to this and other methods for administering compounds in accordance with the methods disclosed herein are further described below.

The disclosed compounds may be used to prepare pharmaceutical compositions for administering in methods of treating symptoms of a psychiatric disorder associated with KCNQ (Kv7) potassium channel activity such as negative symptoms in a patient having schizophrenia or craving in a patient having drug addiction.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disorder. As such, the methods disclosed herein encompass both therapeutic and prophylactic administration.

With respect to treatment, the term "effective amount" refers to the amount or dose of the compound, upon single or multiple dose administration to the subject, which provides the desired effect in the subject under treatment. The disclosed methods may include administering an effective amount of the disclosed compounds (e.g., as present in a pharmaceutical composition) for treating a symptom of a psychiatric disorder whereby the symptom is reduced or prevented.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the blood or bone marrow disease or disorder involved; the response of the individual subject; the particular compound administered; the mode of administration; the bioavailability characteristics of the preparation administered; the dose regimen selected; the use of concomitant medication; and other relevant circumstances.

In some embodiments, a daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment. The dose may be administered under any suitable regimen (e.g., twice daily, daily, or weekly).

In some embodiments, the disclosed compounds may be administered as a pharmaceutical composition that delivers an effective amount of the compound to modulate (e.g., inhibit) KCNQ (Kv7) potassium channel activity. In some embodiments, the amount of the disclosed compounds that is effective to inhibit KCNQ (Kv7) potassium channel activity is about 0.05-50 µM (or about 0.05-10 µM, or about 0.05-1 µM).

The pharmaceutical compositions for use according to the methods as disclosed herein may include be a single compound as an active ingredient or a combination of compounds as active ingredients. For example, the methods disclosed herein may be practiced using a composition containing a single compound that treats symptoms of a psychiatric disorder, or it can be practiced using a composition containing two or more compounds that treat symptoms of a psychiatric disorder. For example, the methods disclosed herein may be practiced using a composition that contains a compound that treats negative symptoms of schizophrenia and further includes a second different compound that treats schizophrenia (e.g., a symptom of schizophrenia such as a positive symptom, a cognitive symptom, or a negative symptom). Additional compounds may include, but are not limited to, chlorpromazine, haloperidol, fluphenazine, promazine, clozapine, sertindole, amisuipride, zotepine, paliperidone (e.g., Invega® brand), risperidone (e.g., Risperdal® brand), aripiprazole (e.g., Abilify® brand), lamotrigine, quetiapine (e.g., Seroquel® brand), perphenazine, flupenthixol, ziprasidone (e.g., Geodon® brand), olanzapine (e.g., Zyprexa® brand), lithium, and valproic acid. In another example, the methods disclosed herein may be practiced using a composition that contains a compound that treats craving in a patient having drug addiction and further includes a second different compound that treats drug addiction (e.g., a symptom of drug addiction such as craving or another symptom of drug addiction). The second different compounds as described above may or may not modulate KCNQ (Kv7) potassium channel activity.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die during manufacturing. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

When it is desired to administer the compound as a suppository, conventional bases can be used. Illustratively, cocoa butter is a traditional suppository base. The cocoa butter can be modified by addition of waxes to raise its melting point slightly. Water-miscible suppository bases, such as polyethylene glycols of various molecular weights, can also be used in suppository formulations.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

As one skilled in the art will also appreciate, the formulation can be prepared with materials (e.g., actives excipients, carriers, diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

The following list of formulations is illustrative. These illustrative formulations may be suitable for preparing pharmaceutical compositions that include compounds which inhibit KCNQ (Kv7) potassium channel activity as "active ingredients" and be administered to treat a psychiatric disorder in a patient in need thereof. The following list of formulations is illustrative and should not be interpreted as limiting the present disclosure or claims in any way:

Formulation 1

Hard gelatin capsules may be prepared using the following ingredients:

|  | Quantity (mg/capsule) |
|---|---|
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

|  | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution may be prepared containing the following components:

|  | Weight % |
|---|---|
| Active Ingredient | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient may be made as follows:

|  |  |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5

Capsules, each containing 80 mg medicament may be made as follows:

|  |  |
|---|---|
| Active Ingredient | 80 mg |
| Starch | 59 mg |

-continued

| | |
|---|---|
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6

Suppositories each containing 225 mg of active ingredient may be made as follows:

| | |
|---|---|
| Active Ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose may be made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl, cellulose and syrup to form a smooth paste. The benzoic acid solution, flavor, and color are diluted with some of the water and added with stirring. Sufficient water is then added to produce the required volume.

Formulation 8

An intravenous formulation containing 100 mg of medicament per 5 ml dose may be prepared as follows:

| | |
|---|---|
| Active Ingredient | 100 mg |
| Mannitol | 100 mg |
| 5 N Sodium hydroxide | 200 ml |
| Purified water to total | 5 ml |

ILLUSTRATIVE EMBODIMENTS

The following embodiments are illustrative and not intended to limit the claimed subject matter.

Embodiment 1. A method for treating a negative symptom of a psychiatric disorder in a patient in need thereof comprising administering an effective amount of a compound that inhibits KCNQ (Kv7) potassium channel activity.

Embodiment 2. The method of embodiment 1, wherein the compound blocks or closes the KCNQ (Kv7) potassium channel or reduces channel function.

Embodiment 3. The method of embodiment 1 or 2, wherein the patient has schizophrenia.

Embodiment 4. The method of embodiment 1, wherein the treated negative symptom includes a symptom selected from a group consisting of flat effect, lack of motivation, anhedonia, diminished speech, social withdrawal, lack of energy, and apathy.

Embodiment 5. The method of embodiment 3 or 4, wherein the method further treats a cognitive symptom and optionally the cognitive symptom is selected from a group consisting of poor executive function, loss of attention and focus, deficits in perception, difficulty in learning, working memory deficits, and problems with short- and long-term memory.

Embodiment 6. The method of any of embodiments 1-5, wherein the compound is Linopirdine.

Embodiment 7. The method of any of embodiments 1-5, wherein the compound is XE991.

Embodiment 8. The method of any of embodiments 1-5, wherein the compound is DMP543.

Embodiment 9. The method of any of embodiments 1-8, further comprising administering an effective amount of a second compound for treating the psychiatric disorder.

Embodiment 10. The method of embodiment 9, wherein the second compound for treating a psychiatric disorder is selected from a group selected from chlorpromazine, haloperidol, fluphenazine, promazine, sulpiride, clozapine, sertindole, amisulpride, zotepine, paliperidone, risperidone, aripiprazole, lamotrigine, quetiapine, perphenazine, flupenthixol, ziprasidone, olanzapine, lithium, and valproic acid.

Embodiment 11. The method of embodiment 10, wherein the second compound is administered concurrently with the effective amount of a compound that inhibits KCNQ (Kv7) potassium channel activity.

Embodiment 12. The method of embodiment 10, wherein the second compound is administered before the effective amount of a compound that inhibits KCNQ (Kv7) potassium channel activity, and optionally, the patient is refractory to treatment with the second compound.

Embodiment 13. The method of embodiment 10, wherein the second compound is administered after the effective amount of a compound that inhibits KCNQ (Kv7) potassium channel activity.

Embodiment 14. A method for treating a symptom of a psychiatric disorder in a patient in need thereof comprising administering an effective amount of DMP543.

Embodiment 15. A method for treating a patient having an addiction to a psychostimulant, optionally cocaine, the method comprising administering an effective amount of a compound that modulates KCNQ (Kv7) potassium channel activity.

Embodiment 16. The method of embodiment 15, wherein the compound blocks or closes the KCNQ (Kv7) potassium channel or reduces the channel function and the method treats craving in the patient.

Embodiment 17. The method of embodiment 15, wherein the compound is administered at a concentration effective for blocking or closing the KCNQ (Kv7) potassium channel.

Embodiment 18. The method of any of embodiments 15-17, wherein the compound is Linopirdine.

Embodiment 19. The method of any of embodiments 15-17, wherein the compound is XE991.

Embodiment 20. The method of any of embodiments 15-17, wherein the compound is DMP543.

Embodiment 21. A method of screening for compounds that treat negative symptoms of schizophrenia by identifying compounds that inhibit KCNQ (Kv7) potassium channel activity.

Embodiment 22. A method of screening for compounds to treat drug addiction in a patient by identifying compounds that inhibit KCNQ (Kv7) potassium channel activity.

Embodiment 23. A method of screening for compounds that treat craving in a patient having drug addiction by identifying compounds that inhibit KCNQ (Kv7) potassium channel activity.

Embodiment 24. The methods of any of embodiments 21-23, wherein KCNQ (Kv7) potassium channel activity is assessed by measuring potassium ion current.

Embodiment 25. The method of any of embodiments 21-23, wherein identifying compounds that inhibit KCNQ (Kv7) potassium channel activity comprises identifying compounds that displace a channel binding compound.

Embodiment 26. The method of embodiment 25, wherein the channel binding compound comprises a label (e.g., a fluorophore or an isotope) and displacement is monitored via the label.

Embodiment 27. The method of embodiment 26, wherein the label is an isotope and displacement of the channel binding compound is monitored using radioactivity measurements, such as scintillation counting in a filter-binding assay.

Embodiment 28. The method of embodiment 26, wherein the label is an isotope and displacement of the channel binding compound is monitored using nuclear magnetic resonance (e.g., monitoring change in line-width upon displacement).

Embodiment 29. The method of embodiment 28 wherein $^{19}$F NMR is used to monitor displacement.

Embodiment 30. The method of any of embodiments 25-30, where the channel binding compound is DMP543, optionally labeled with an isotope or a fluorophore.

EXAMPLES

The following example is illustrative and not intended to limit the claimed subject matter.

Example

The KCNQ (Kv7) Potassium Channel as a Target for Treatment of Psychiatric Disorders Such as Schizophrenia Introduction Schizophrenia is a chronic mental disorder with devastating and disruptive personal, family, and social consequences, which affects about 1.1% of the world population above 18 years of age. In any give year, more than 3 million Americans and more than 68 million individuals in the world suffer from pathologies associated with schizophrenia. The development of antipsychotic medications starting in early 1950s (first generation or typical antipsychotics) provided the pharmacological tools to manage some of the symptoms although significant side effects exist. The development of the second generation antipsychotics (the atypical antipsychotics) starting in early 1990s provided better treatment options for patients due to reduced Parkinsonian movement side effects; however, significant side effects (such as weight gain, sexual dysfunction) and increased risk for pathologies such as diabetes, cardiovascular complications such as heart attack, heart failure, stroke, and death in the elderly has limited the usefulness of these medications (Lieberman et al., 2005, The New England Journal of Medicine, vol. 353, pp. 1209-1223). Currently, FDA requires black box warning label for all antipsychotics on the market. Moreover, the advantages of the second generation antipsychotics over the older first generation drugs in treating the symptoms have been questioned and are under scrutiny at this time (see Lieberman et al., 2005, The New England Journal of Medicine, vol. 353, pp. 1209-1223 and references therein). Regardless of the outcome of these scientific debates, patient history indicates that more than 70% of patients taking either first or second generation antipsychotics become non-compliant before 18 months of treatment mainly due to severe and disruptive side effects (Lieberman et al., 2005, The New England Journal of Medicine, vol. 353, pp. 1209-1223). Most importantly, although these drugs do ameliorate the positive symptoms of schizophrenia (hallucination, delusion, disorganized speech), they are not effective against the negative (loss of interest, emotion, motivation, and social withdrawal) and cognitive (attention and memory deficits, thought disorder) deficits of schizophrenia (Lieberman et al., 2005, The New England Journal of Medicine, vol. 353, pp. 1209-1223). Unfortunately, there is no effective treatment available for the negative and cognitive symptoms. However, treatment of negative and cognitive symptoms is pivotal in managing the behavioral symptoms of schizophrenia because they are chronically present and exacerbate with age (Fenton and McGlashan, (1991), Arch. Gen. Psychiatry, vol. 48, pages 978-986). The development of medications for treatment of the negative and cognitive symptoms with no or minor side effects is an important goal in the treatment of schizophrenia and will have a significant impact on the management of the disease and patients' quality of live.

The neurobiological basis of schizophrenia is not known, but has been hypothesized to arise, at least partly, from altered dopamine, serotonin and glutamate neurotransmission and signaling in the forebrain regions including, but not limited to, prefrontal cortex and nucleus accumbens. Accordingly, there has been a great interest to understand the nature of these abnormalities in the brain and develop agents capable of modulating neurotransmission and signaling in the brain.

Here, a novel mechanism in the brain has been identified, the KCNQ (Kv7) potassium channels, capable of modulating neurotransmission and signaling. The KCNQ (Kv7) potassium channel is a low-threshold, voltage-dependent, non-inactivating potassium channel in neurons. It has been shown that reconstitution of the two potassium channel subunits, KCNQ2 and KCNQ3 can regenerate the KCNQ (Kv7) channel and the M-current in neurons. The KCNQ (Kv7) potassium channel slowly activates when an excitatory stimulus depolarizes the neuron, repolarizing the membrane back toward resting potential and suppressing firing. These channels are expressed at high levels in neurons of cortex, striatum and nucleus accumbens. Because potassium channels can regulate cell excitability and neurotransmitter release, the KCNQ channels may play an important role in regulating dopaminergic and glutamatergic signaling and neurotransmitter release in the brain. The unique properties of this mechanism may be beneficial in ameliorating the clinical symptoms of schizophrenia. The data presented here supports this notion and further suggest that this mechanism may be a suitable target for development of pharmacotherapy for schizophrenia. A pivotal advantage of the KCNQ (Kv7) potassium channels is that compounds effective at this ion channel have previously been through clinical trials for another disease (Alzheimer's disease) and do not show toxicity or serious side effects.

The KCNQ potassium channels were first described in 1980 as a novel subthreshold potassium channel with unique properties of slow activation and non-deactivation which render these channels particularly effective at regulating the neuronal membrane potential, generation of action potentials, and neurotransmitter release (Brown and Adams (1980)

Nature, vol 283, page 673-676). The family of KCNQ potassium channels (Kv7 or M-current) are encoded by 5 genes (Kv7.1-Kv7.5) and it was determined that channel complexes made up of KCNQ2 (Kv7.2) and KCNQ3 (Kv7.3) proteins can reproduce the channel properties observed in vivo (Wang et al. (1998) Science, vol 282, page 1890-1893). In vitro and in vivo neurotransmitter release studies have shown that blockade of these potassium channels does not modulate the basal extracellular levels of neurotransmitters, but enhances stimulus-evoked ($K^+$-stimulated) release of dopamine, serotonin, acetylcholine and glutamate in striatum and cortex (Zaczek et al. (1998) JPET, vol 285, pages 724-730). Based on the ability of these channels to release neurotransmitters in hippocampus and cortex, especially acetylcholine, it was hypothesized that the channel blockers may be beneficial in treatment of Alzheimer's memory deficits (Zaczek et al. (1998) JPET, vol 285, pages 724-730). The first generation (Linopirdine) and the second generation of channel blockers (XE991, DMP543) were developed by DuPont Pharmaceuticals. Linopirdine and DMP543 were tested in clinical trials, which entered into the phase 3 but the clinical data for improvement of Alzheimer's symptoms proved to be equivocal and, therefore, the development of these compounds were terminated in year 2000 (Zaczek et al. (1998) JPET, vol 285, pages 724-730). However, completion of clinical phase 3 and extensive data in literature indicate that both generation of compounds are bioavailable, do not exhibit toxicity, serious side effects and are well tolerated in adults. The DMP543 has higher potency at KCNQ channel, higher serum half-life, and higher duration of action (Zaczek et al. (1998) JPET, vol 285, pages 724-730).

The ability of KCNQ channel blockers to depolarize membrane potentials and increase neuronal activity combined with the capacity to augment stimulus-evoked neurotransmitter release in absence of changes in the basal levels points to a possible therapeutic value for the KCNQ potassium channels. The present inventor hypothesized that the combination of increased neuronal activity and evoked neurotransmitter release in the brain would benefit the negative and cognitive symptoms present in schizophrenia and craving in addiction. It has been suggested that these properties of the KCNQ channel may enhance signal-to-noise ratio in neuronal circuits benefiting cognitive processes (Zaczek et al. (1998) JPET, vol 285, pages 724-730). This hypothesis was examined using the acute phencyclidine (PCP) administration animal model of schizophrenia in rodents. The results of these studies indicate that the KCNQ potassium channels present a novel therapeutic target for the treatment of positive, negative and cognitive deficits of schizophrenia and craving in addiction.

Results

Figure 2:
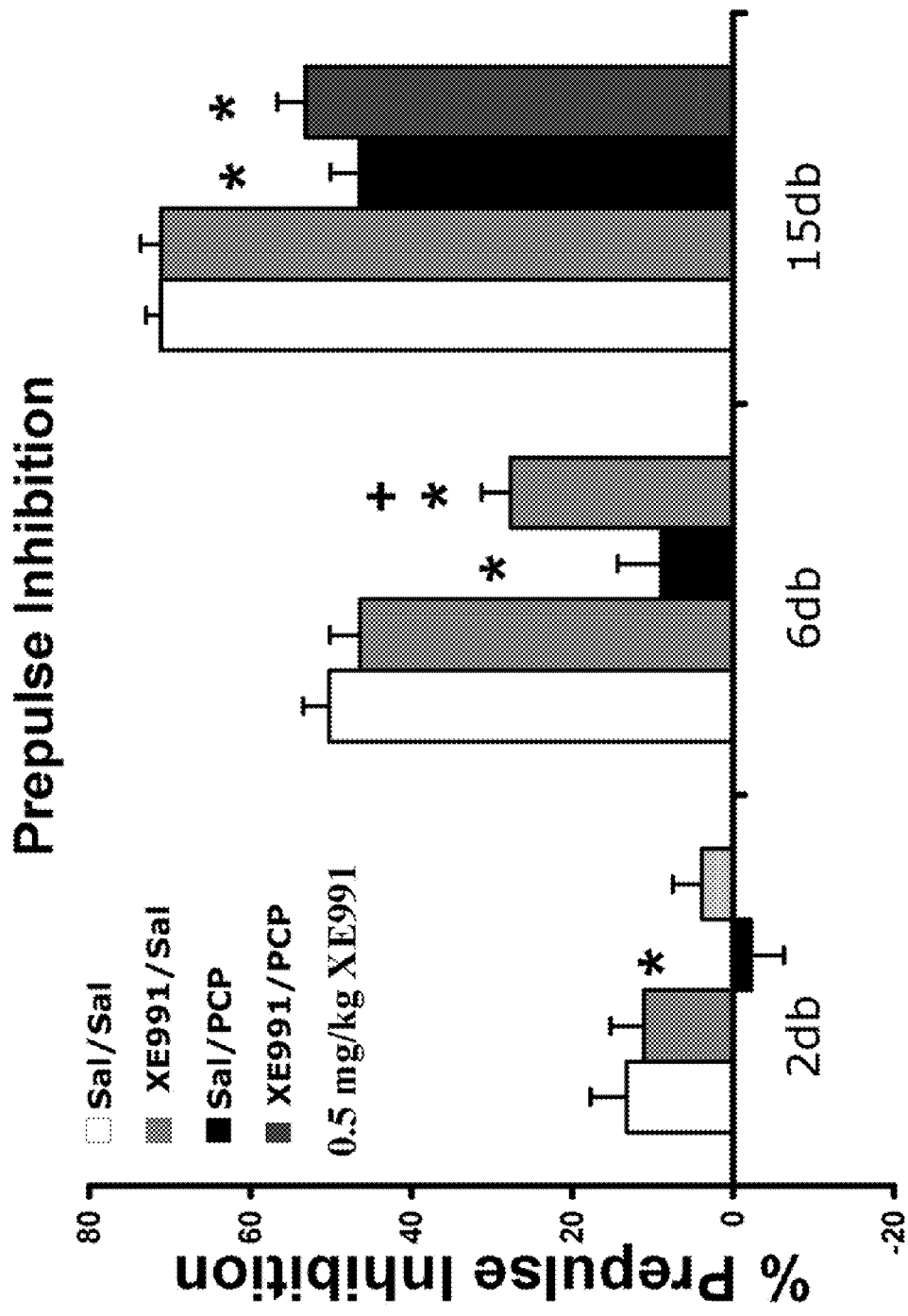
FIG. 2. shows that acute administration of PCP (1.5 mg/kg, sc) disrupts the prepulse inhibition (PPI) of the startle response and this effect is reversed after the blockade of the KCNQ (Kv7) potassium channels by XE991.

FIG. 2 shows that an acute administration of PCP (1.5 mg/kg, sc) disrupted the prepulse inhibition (PPI) of the startle response and this effect was reversed after the blockade of the KCNQ potassium channels. The startle response is produced by delivery of a sudden and intense sensory stimulus pulse (120 db sound) and can be inhibited by exposure to a weaker prepulse (62, 66, or 75 db) which is slightly above the background noise level (60 db). The inhibitory effect of the prepulse on pulse-mediated startle response is an example of sensorimotor gating or filtering mechanism which has been shown to be deficient in schizophrenia patients and can be induced in healthy individuals by noncompetitive NMDA glutamate receptor antagonists such as PCP and Ketamine. PPI has been used as a measure of sensory information processing in rodents and humans. The data in FIG. 2 shows that animals treated with saline or KCNQ channel blocker XE991 (0.5 mg/kg, s.c.) 10 minutes before placing into the startle chamber did not show any disruption of the prepulse inhibition at any of the three prepulse intensities. Therefore, the channel blocker alone did not have any disruptive effect on PPI. However, as expected, PCP (1.5 mg/kg, s.c.) reduced the prepulse inhibition at all three prepulses. The blockade of KCNQ channels by systemic administration of XE991 (0.5 mg/kg, s.c.) reversed the PCP-induced deficits in PPI using the 66 db prepulse (shown in FIG. 2 as 6 db above background noise, 60 db). A cocktail mixture of XE991 and PCP dissolved in saline was used in these studies. N=38 rats per treatment. *$p<0.05$ vs. Sal/Sal; +$p<0.05$ vs. Sal/PCP.

Figure 3:
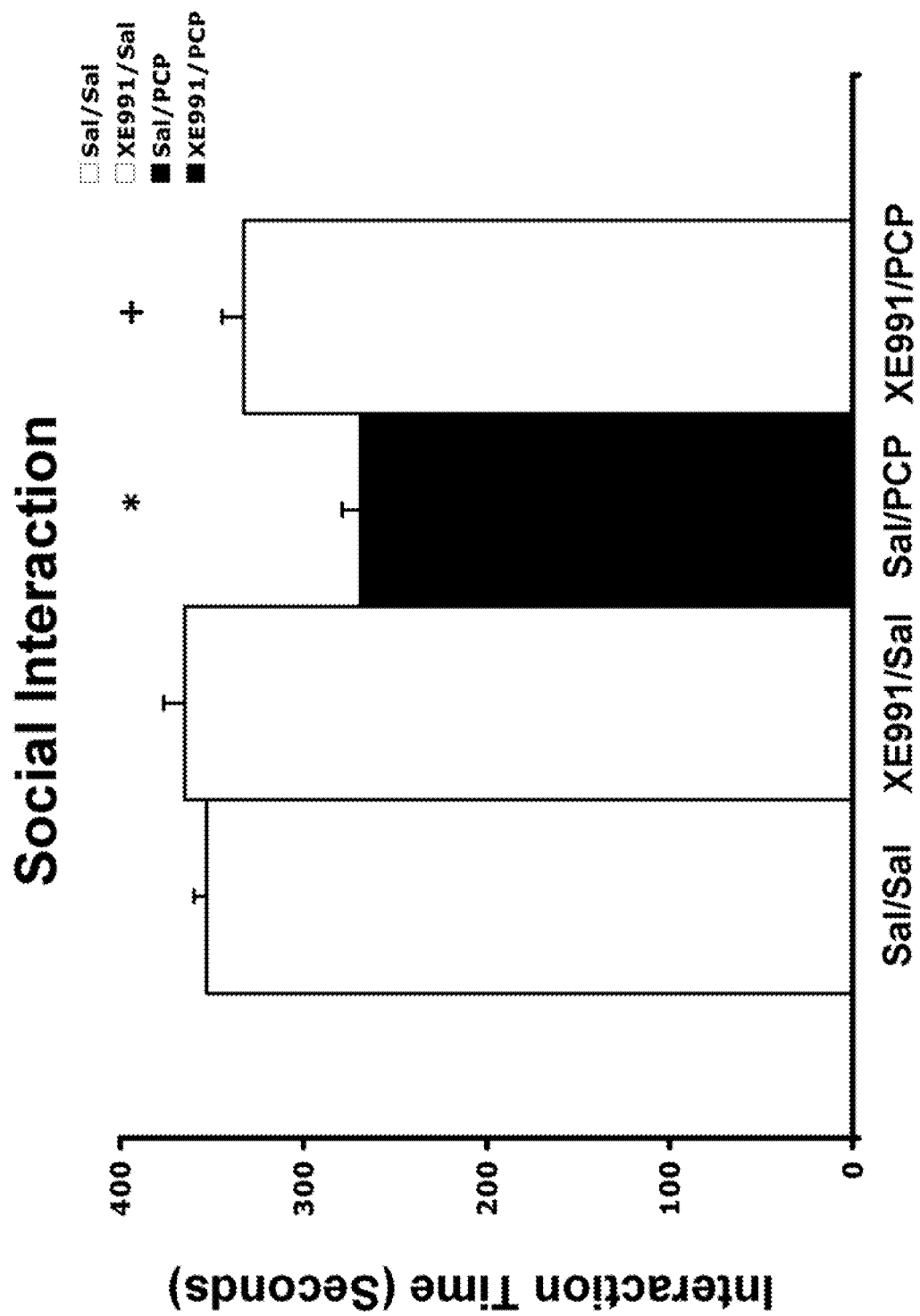
FIG. 3. shows that the disruptive effect of PCP (1.5 mg/kg, sc) on social interaction behavior is reversed after blockade of the KCNQ (Kv7) potassium channels by XE991.

FIG. 3 shows that the disruptive effect of PCP (1.5 mg/kg, s.c.) on social interaction behavior is reversed after blockade of the KCNQ channels by XE991. Social interaction deficit is considered to be a negative symptom of schizophrenia and can be induced in rodents by acute PCP or Ketamine administration and can be reversed by antipsychotics. The data in FIG. 3 shows that acute saline or XE991 (0.5 mg/kg, s.c.) treatment 15 minutes before placement into the social interaction arena did not significantly modulate the level of social interaction between one pair of animals. Therefore, XE991 alone did not produce any effects. However, acute PCP administration (1.5 mg/kg, s.c., 15 minutes before testing) produced a significant reduction in social interaction time. The co-administration of KCNQ channel blocker XE991 (0.5 mg/kg, s.c.) with PCP (1.5 mg/kg, s.c.) reversed the deficit produced by PCP alone. A cocktail mixture of XE991 and PCP dissolved in saline was used in these studies. *$p<0.05$ vs. Sal/Sal; +$p<0.05$ vs. Sal/PCP; N=25-42 rats per treatment.

Figure 4:
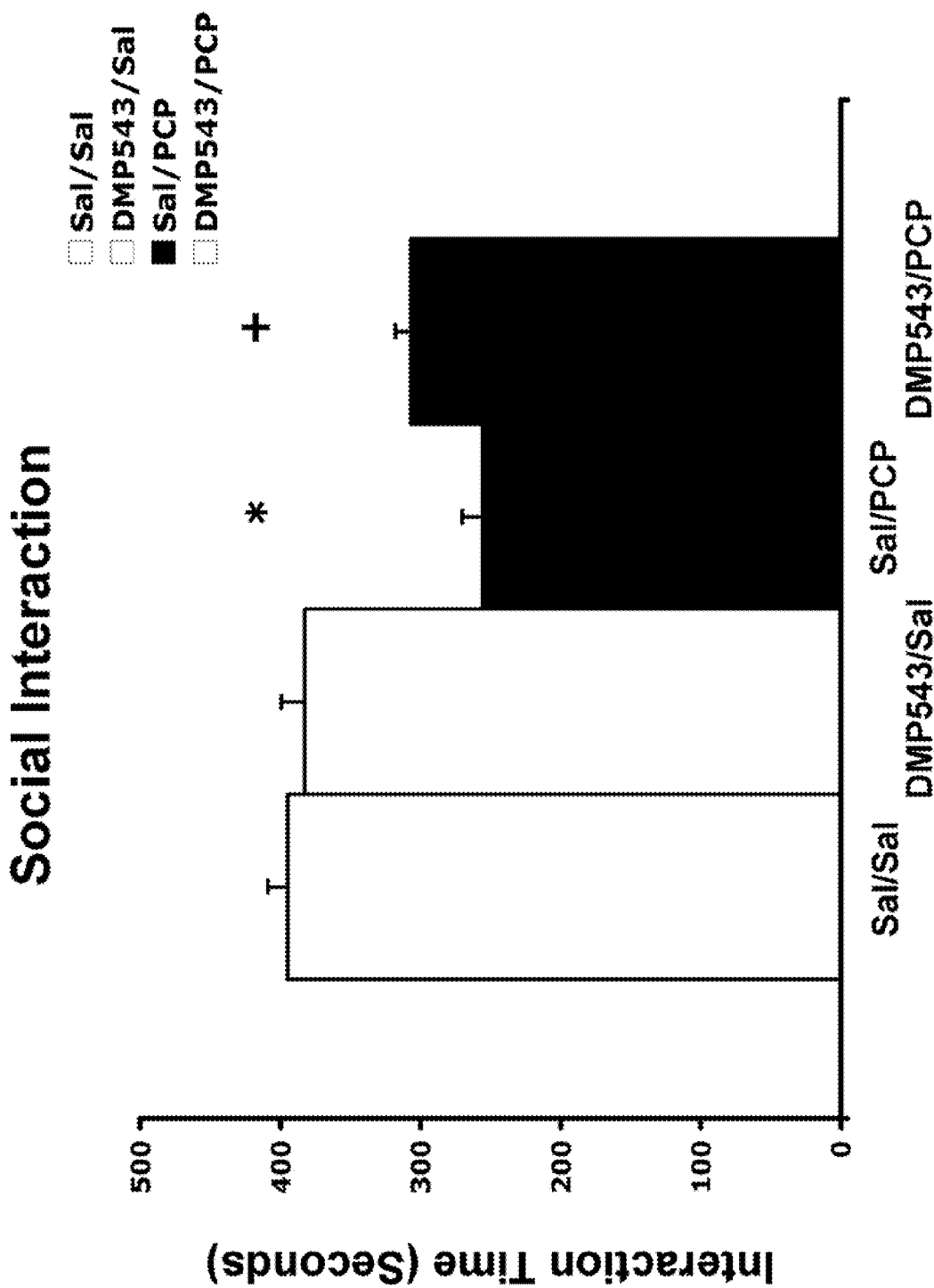
FIG. 4 shows that the disruptive effect of PCP (1.5 mg/kg, s.c.) on social interaction behavior is reversed after blockade of the KCNQ (Kv7) potassium channels by DM543.

FIG. 4 shows that the disruptive effect of PCP (1.5 mg/kg, s.c.) on social interaction behavior is reversed after blockade of the KCNQ channels by DMP543. Social interaction deficit is considered to be a negative symptom of schizophrenia and can be induced in rodents by acute PCP or Ketamine administration and can be reversed by antipsychotics. The data in FIG. 4 shows that acute saline or DMP543 (0.15 mg/kg, s.c.) treatment 15 minutes before placement into the social interaction arena did not significantly modulate the level of social interaction between one pair of animals. Therefore, DMP543 alone did not produce any effects. However, acute PCP administration (1.5 mg/kg, s.c., 15 minutes before testing) produced a significant reduction in social interaction time. The co-administration of KCNQ channel blocker DMP543 (0.15 mg/kg, s.c.) with PCP (1.5 mg/kg, s.c.) significantly reversed the deficit produced by PCP alone. A cocktail mixture of DMP543 and PCP dissolved in 40% DMSO was used in these studies. *$p<0.05$ vs. Sal/Sal; +$p<0.05$ vs. Sal/PCP; N=10-28 rats per treatment.

Figure 5:
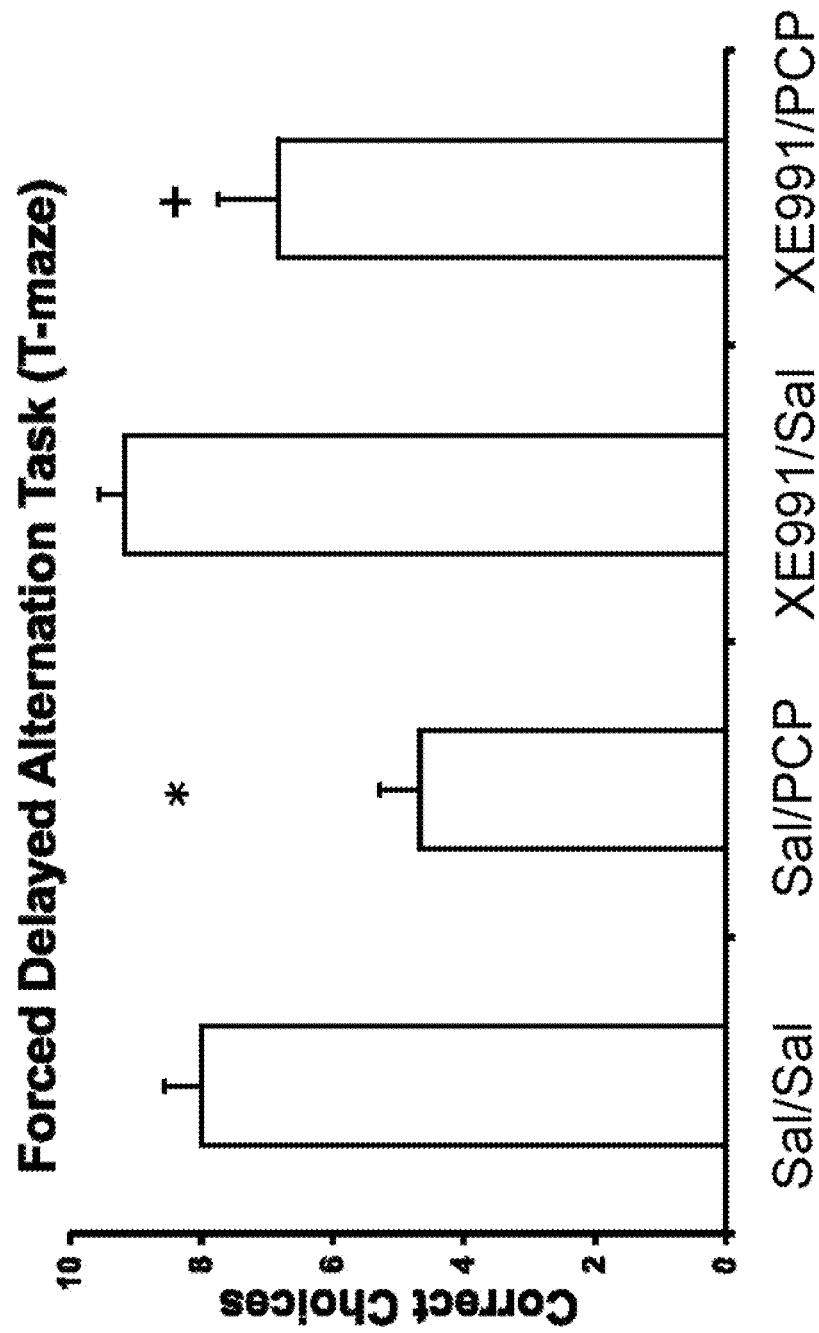
FIG. 5. shows that blockade of KCNQ potassium channels in prefrontal cortex (PFC) reversed the working memory deficits produced by acute PCP (3 mg/kg, i.p.) administration as determined by forced delayed alternation task in a T-maze.

FIG. 5 shows that blockade of KCNQ channels in prefrontal cortex (AFC) reversed the working memory deficits produced by acute PCP administration as determined by forced delayed alternation task in a T-maze. This experimental paradigm involves the working memory, a prefrontal cortex dependent task, and is used to examine attention and memory function. This study was conducted to determine the role of KCNQ channels in PFC in regulation of memory. The data in FIG. 5 show that acute bilateral infusion of saline (1 ul/1 min) or XE991 (60 nmol/1 ul/1 min) into the prefrontal cortex did not disrupt the memory and performance of the animal in delayed alternation task. Therefore, treatment with XE991 alone did not produce any effect on its own. However, acute PCP (3.0 mg/kg, s.c.) administration one hour before behavioral testing produced a robust and reproducible disruption of working memory in the trained rats. Pretreatment of PFC with a microinfusion of XE991 (60 nmol/1 µl/1 min; 5 minutes before PCP administration) reversed the PCP-induced memory deficits. Moreover, there was no effect of XE991 on PCP-mediated working memory disruption when the channel blocker was microinjected in the nucleus accumbens (data not shown) suggesting that the pharmacological effects of the channel modulation may primarily be located in prefrontal cortex in agreement with the known role of PFC in working memory. N=16 rats per treatment. *p<0.05 vs. Sal/Sal; +p<0.05 vs. Sal/PCP.

Summary and Conclusions

The results presented here indicate that KCNQ (Kv7) potassium channels are desirable molecular targets for development of pharmacotherapies for the treatment of the clinical symptoms of schizophrenia and drug addiction. These novel properties involve unique physiological function of the KCNQ (Kv7) family of the potassium channels in the brain. Furthermore, the results demonstrate the roles of these channels in the brain as illustrated by the behavioral pharmacology investigations. The data indicate that channel openers and blockers can be utilized to ameliorate behaviors in laboratory rat models for (a) positive, negative, or cognitive deficit symptoms of schizophrenia in humans; and (b) behavioral symptoms of addiction. To the best of the inventor's knowledge, it has never been recognized or suggested that KCNQ channel closers could be used to treat negative symptoms of schizophrenia (ex. loss of emotion, loss of interest, loss of motivation, social withdrawal) or the cognitive deficits of schizophrenia (ex. information processing, working memory, executive function) or the behavioral symptoms associated with addiction such as craving. The present discovery of the utility of KCNQ channel blockers to treat these symptoms of schizophrenia and addiction is both valuable and unexpected. The potential application of these properties for development of pharmacotherapies goes beyond these two pathologies because these properties may also be beneficial in other pathologies that may benefit from modulation of dopamine and glutamate signaling such as Post-Traumatic Stress Disorder (PTSD) and major depressive disorder (depression).

The data suggests that targeting the KCNQ (Kv7) potassium channels may be an effective strategy in identifying and developing drugs that have the potential to significantly improve symptoms of schizophrenia and provide an effective treatment for psychostimulant addiction. Furthermore, the data suggest a previously unrecognized use for existing drugs that operate as KCNQ channel closers.

Specifically, the results indicate that DMP543, XE991 or Linopirdine (three channel blockers or closers) can attenuate or fully reverse the deficits in the forced delayed alternation task performance in a T-maze, social interaction, and prepulse inhibition produced by phencyclidine administration in laboratory rodents. This rodent model is used to assess and model aspects of cognitive performance, social withdrawal, and sensory processing. The above mentioned impairments have been reported to occur in schizophrenia patients, and include the negative symptoms and cognitive deficits of schizophrenia, which are currently not treated adequately by existing medications. All clinically-relevant findings described above are highly novel, and strongly suggest that the KCNQ (Kv7) potassium channels represent a unique target in the treatment of schizophrenia and addiction.

Methods

Microinjection and Behavioral Experiments. Stainless Steel cannulae were implanted bilaterally 1 mm above nucleus accumbens or implanted in prefrontal cortex. Rats were permitted a minimum of 7 days recovery from surgery. Drugs were injected using an injection needle that extended 1 mm beyond the tip of the guide cannulae. The volume of injection was 1 µl for Linopirdine and XE991 and 0.5 µl for other drugs and was delivered over 1 minute. In experiments where two drugs were delivered into accumbens, the microinjections were separated by 15 minutes. Behavioral activity then was monitored as discussed in the Results.

Drugs. All drugs were purchased from commercial sources and dissolved in saline. Linopirdine, XE991, and DMP543 were initially dissolved in 100% DMSO and diluted to final concentration of 25% DMSO (Linopirdine) and 40% (XE991 and DMP543). All drug doses were nmol per side and were injected bilaterally into the specified brain region.

REFERENCES

Bakshi V P, Geyer M A (1997) Phencyclidine-induced deficits in prepulse inhibition of startle are blocked by prazosin, an alpha-1 noradrenergic antagonist. *J. Pharmacal. Exp. Ther,* 283, 666-674.

Brown D A, Adams P R (1980) Muscarinic suppression of a novel voltage-sensitive K+ current in a vertebrate neurone. *Nature* 283, 673-676.

Earl R A, Zaczek R, Teleha C A, Fisher B N, Maciag C M, Marynowski M E, Logue A R, Tam S W, Tinker W J, Huang S M, Chorvat R J (1998) 2-Fluoro-4-pyridinylmethyl analogues of linopirdine as orally active acetylcholine release-enhancing agents with good efficacy and duration of action. *J. Med. Chem.* 41, 4615-4622.

Elmedyb P, Calloe K, Schmitt N, Hansen R S, Grunnet M, Olesen S P (2007) Modulation of ERG channels by XE991. *Basic & Clinical Pharmacol. & Toxicol.* 100, 316-322.

Fenton W S, McGlashan T H (1991) Natural history of schizophrenia subtypes. II. Positive and negative symptoms and long-term course. *Arch. Gen. Psychiatry* 48, 978-986.

Lieberman J A, Stroup T S, McEvoy J P, Swartz M S, Rosenheck R A, Perkins D O, Keefe R S, Davis S M, Davis C E, Lebowitz B D, Severe J, Hsiao J K; Clinical Antipsychotic Trials of Intervention Effectiveness (CATIE) Investigators (2005) Effectiveness of antipsychotic drugs in patients with chronic schizophrenia. *N. Engl. Med.* 353, 1209-1223.

Saganich M J, Machado E, Rudy B (2001) Differential expression of genes encoding subthreshold-operating voltage-gated K+ channels in brain. *J. Neurosci.* 21, 4609-4624.

Schnee M E, Brown B S (1998) Selectivity of linopirdine (DuP 996), a neurotransmitter release enhancer, in blocking voltage-dependent and calcium-activated potassium currents in hippocampal neurons. *J. Pharmacol. Exp. Ther.* 286, 709-717.

Tam S W (1983) Naloxone-inaccessible sigma receptor in rat central nervous system. *Proc. Nall. Acad. Sci.* 80, 6703-6707.

Tam S W, Rominger D, Nickolson V J (1991) Novel receptor site involved in enhancement of stimulus-induced acetylcholine, dopamine, and serotonin release. (1991) *Mol. Pharmacol.* 40, 16-21.

Wang Q, Curran M E, Splawski I, Burn T C, Millholland J M, VanRaay T J, Shen J, Timothy K W, Vincent G M, de Jager T, Schwartz P J, Toubin J A, Moss A J, Atkinson D L, Landes G M, Connors T D, Keating M T (1996) Positional cloning of a novel potassium channel gene: KVLQT1 mutations cause cardiac arrhythmias. *Nat. Genet.* 12, 17-23.

Wang H S, Brown B S, McKinnon D, Cohen I S (2000) Molecular basis for differential sensitivity of KCNQ and I(Ks) channels to the cognitive enhancer XE991. *Mol. Pharmacol.* 57, 218-1223.

Wang H S, Pan Z, Shi W, Brown B S, Wymore R S, Cohen I S, Dixon J E, McKinnon D (1998) KCNQ2 and KCNQ3 potassium channel subunits: molecular correlates of the M-channel. *Science* 282, 1890-1983.

Zaczek R, Chorvat R J, Saye J A, Pierdomenico M E, Maciag C M, Logue A R, Fisher B N, Rominger D H, Earl R A (1998) Two new potent neurotransmitter release enhancers, 10,10-bis(4-pyridinylmethyl)-9(10H)-anthracenone and 10,10-bis(2-fluoro-4-pyridinylmethyl)-9(10H)-anthracenone: comparison to linopirdine. *J. Pharmacol. Exp. Ther.* 285, 724-730.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. A method for treating a negative symptom of a psychiatric disorder in a psychiatric patient exhibiting the negative symptom, the method comprising administering an effective amount of a compound that inhibits KCNQ (Kv7) potassium channel activity to the psychiatric patient exhibiting the negative symptom, wherein the compound is linopirdine, XE991, DMP543, or a deuterated derivative or analog thereof.

2. The method of claim 1, wherein the patient has schizophrenia.

3. The method of claim 2, Wherein the treated negative symptom includes a symptom selected from the group consisting of flat affect, lack of motivation, anhedonia, diminished speech, social withdrawal, lack of energy, and apathy.

4. The method of claim wherein the method further treats a cognitive symptom of the psychiatric disorder in the patient.

5. The method of claim 4, wherein the treated cognitive symptom includes a symptom selected from et the group consisting of poor executive function, loss of attention and focus, deficits in perception, difficulty in learning, working memory deficits, and problems with short- and long-term memory.

6. The method of claim 1, further comprising administering an effective amount of a second compound for treating the psychiatric disorder.

7. The method of claim 6, wherein the second compound for treating a psychiatric disorder is selected from the group selected from chlorpromazine, haloperidol, fluphenazine, promazine, sulpiride, clozapine, sertindole, amisulpride, zotepine, paliperidone, risperidone, aripiprazole, lamotrigine, quetiapine, perphenazine, flupenthixol, ziprasidone, olanzapine, lithium, and valproic acid.

8. The method of claim 6, wherein the second compound is administered concurrently with the compound that inhibits KCNQ (Kv7) potassium channel activity.

9. The method of claim 6, wherein the second compound is administered before the effective amount of a compound that inhibits KCNQ (Kv7) potassium channel activity, and optionally, the patient is refractory to treatment with the second compound.

10. The method of claim 6, wherein the second compound is administered after the effective amount of a compound that inhibits KCNQ (Kv7) potassium channel activity.

11. The method of claim 6, wherein the second compound treats a cognitive symptom of the psychiatric disorder in the patient or the second compound treats a positive symptom of the psychiatric disorder in the patient.

12. The method of claim 1, wherein the compound is linopirdine or a deuterated derivative or analog thereof.

13. The method of claim 1, wherein the compound is XE991 or a deuterated derivative or analog thereof.

14. The method of claim 1, wherein the compound is DMP543 or a deuterated derivative or analog thereof.

* * * * *

UNITED STATES PATENT AND TRADEMARK OFFICE
CERTIFICATE OF CORRECTION

| | | |
|---|---|---|
| PATENT NO. | : 9,017,735 B2 | |
| APPLICATION NO. | : 12/793330 | |
| DATED | : April 28, 2015 | |
| INVENTOR(S) | : Mohammadhossein Behnam Ghasemzadeh | |

It is certified that error appears in the above-identified patent and that said Letters Patent is hereby corrected as shown below:

In the Specification

Col 1, lines 15-20 should read as follows:

STATEMENT REGARDING U.S. GOVERNMENT SPONSORED RESEARCH OR DEVELOPMENT

This invention was made with U.S. government support under Grant No. DA14328 from the National Institutes of Health. The U.S. government has certain rights in this invention.

Signed and Sealed this
Twenty-fifth Day of August, 2015

Michelle K. Lee
*Director of the United States Patent and Trademark Office*